United States Patent [19]

Berges

[11] 4,007,178
[45] Feb. 8, 1977

[54] O-ACYL-7-ACYLAMINOCEPHALOS-PORADESIC ACIDS

[75] Inventor: David A. Berges, Audubon, Pa.

[73] Assignee: SmithKline Corporation, Philadelphia, Pa.

[22] Filed: May 15, 1975

[21] Appl. No.: 577,816

Related U.S. Application Data

[60] Division of Ser. No. 255,632, May 22, 1972, Pat. No. 3,905,967, which is a continuation-in-part of Ser. No. 141,380, May 7, 1971, abandoned.

[30] Foreign Application Priority Data

Apr. 10, 1972  United Kingdom ............. 16342/72

[52] U.S. Cl. ...................... 260/243 C; 260/308 R; 260/309
[51] Int. Cl.² ...................................... C07D 501/34
[58] Field of Search ............................... 260/243 C

[56] References Cited

UNITED STATES PATENTS

| | | | |
|---|---|---|---|
| 3,849,408 | 11/1974 | Dolfini ........................... | 260/243 C |
| 3,852,277 | 12/1974 | Jacobus et al. ................ | 260/243 C |
| 3,878,203 | 4/1975 | Christenson et al. .......... | 260/243 C |
| 3,907,784 | 9/1975 | Huffman ....................... | 260/243 C |

FOREIGN PATENTS OR APPLICATIONS

6,801,765   6/1967   Australia ...................... 260/243 C

*Primary Examiner*—Donald G. Daus
*Assistant Examiner*—David E. Wheeler
*Attorney, Agent, or Firm*—Joan S. Keps; Richard D. Foggio; William H. Edgerton

[57] ABSTRACT

A method for O-acylating the 3-hydroxymethyl group of 7-acylaminocephalosporadesic acids by reaction with an azolide and new O-acyl-7-acylaminocephalosporadesic acids in which the O-acyl group is derived from an alkoxyalkanoic acid or an amino acid.

5 Claims, No Drawings

O-ACYL-7-ACYLAMINOCEPHALOSPORADESIC ACIDS

This is a division of application Ser. No. 255,632 filed May 22, 1972, now U.S. Pat. No. 3,905,967, which is a continuation-in-part of Ser. No. 141,380 filed May 7, 1971, now abandoned.

This invention relates to a method for the preparation of O-acyl-7-acylaminocephalosporadesic acids, in particular to the step in that method which comprises O-acylating the 3-hydroxymethyl group of 7-acylaminocephalosporadesic acids. In addition, this invention relates to new O-acyl-Lb 7-acylaminocephalosporadesic acids, in particular to compounds in which the O-acyl group is derived from an alkoxyalkanoic acid or an amino acid.

The 3-hydroxymethyl group of cephalosporadesic acids is known to be difficult to acylate. Lactone formation or isomerization to the $\Delta^2$-isomers is reported to occur during attempted O-acylations. E. Van Heyningen, *Advances in Drug Research*, Volume 4, pages 28–29 (1967). This invention provides a method of preparing a wide variety of O-acyl-7-acylaminocephalosporadesic acids in good yield.

O-Acyl-7-acylaminocephalosporadesic acids having antibacterial activity are prepared by the method of this invention According to the method of this invention, the 3-hydroxymethyl group of 7-acylaminocephalosporadesic acids is O-acylated by reaction with an azolide at about 0° to 50° C. The term "azolide" denotes an N-acyl heterocycle, the heterocycle being a quasi-aromatic five-membered ring containing at least two nitrogen atoms. Staab, *Angew. Chem. Internat. Edit.*, 1:351 (1962). Preferably, the azolide is an N-acylimidazole, 1-acyl-1,2,4-triazole or 1-acyl-1,2,3-triazole. Advantageously, the azoide is an N-acylimidazole.

The method according to this invention is represented as follows:

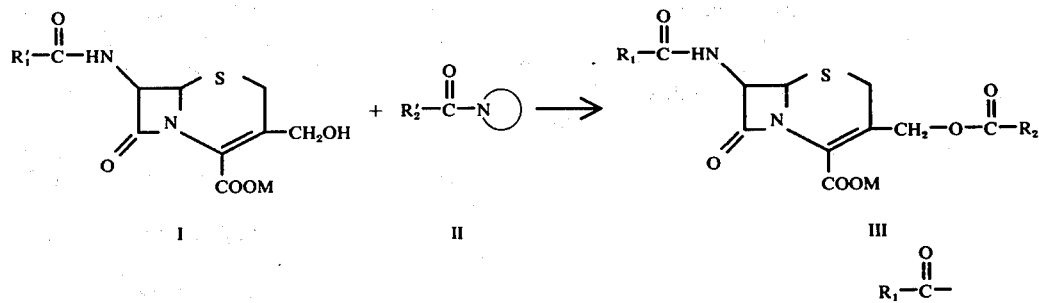

in which:

is an acyl group for antibacterial cephalosporins;

is the same as

except that any hydroxy, amino or carboxy groups have protecting groups;

is an acyl group for antibacterial cephalosporins, except that an easily eliminated $\beta$-substituent is not present;

is the same as

except that any hydroxy, amino and thiol groups have protecting groups;

is a quasi-aromatic five-membered ring containing at least two nitrogen atoms; and M is hydrogen, an alkali metal cation or a quaternary ammonium cation.

In formula III above,

represents any of the variety of acyl groups which may be present on the 7-amino group of antibacterial cephalosporins. There are many examples of such acyl groups in the prior art. $R_1$ may represent, for example, substituted-alkyl, an aralkyl or a heteroalkyl group. Exemplary of some of the acyl groups which are present on the 7-amino group of known antibacterial cephalosporins are the following:

$R_1$ is benzyl

α-hydroxybenzyl
α-aminobenzyl
α-aminocyclohexadienylmethyl
thienylmethyl
α-hydroxythienylmethyl
α-aminothienylmethyl
tetrazolylmethyl
pyridylthiomethyl
phenoxymethyl
phenylthiomethyl
benzofurylmethyl
isothiazolylmethyl
α-methoxy-3,4-dichlorobenzyl
cyanomethyl
sydnonemethyl In Formula III above,

represents any acyl group which may be present as an O-substituent on the 3-hydroxymethyl group of antibacterial cephalosporins and which is derived from a carboxylic acid of the formula

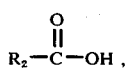

which is capable of forming an azolide of the formula

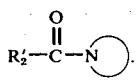

$R_2$, therefore, cannot contain an easily eliminated β-substituent such as halo. Exemplary of groups represented by $R_2$ are lower alkyl, aryl, aralkyl, heteroaryl and heteroaralkyl. These groups may have substituents and functional groups (other than easily eliminated β-substituents) such as amino, mercapto, alkylmercapto, hydroxy, alkoxy and carboxy. Examples of $R_2$ groups, all of which may be substituted as outlined above, are the following:

lower alkyl having 1-6 carbon atoms, straight chain or branched
phenyl
naphthyl
benzyl
thienyl
furyl The process of this invention is preferably carried out at neutral to mildly basic pH in an inert solvent, such as tetrahydrofuran, benzene, chloroform or preferably, dimethylformamide. The reaction is carried out at about 0° to 50° C., preferably at room temperature. Conveniently, the progress of the reaction is monitored and its completion is determined by thin-layer chromatography.

The 7-acylaminocephalosporadesic acid is preferably used in the process of this invention in the form of an alkali metal salt.

The azolide is prepared by reacting a carboxylic acid with a diazolide of carbonic acid. This process is represented as follows:

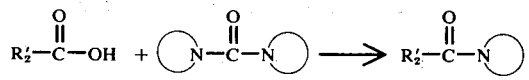

in which $R_2'$ is as defined above.

This reaction is preferably carried out in an inert solvent such as tetrahydrofuran, benzene, chloroform or preferably, dimethylformamide, at about room temperature. Conveniently, the resulting azolide is not isolated but is used in the resulting solution in the O-acylation process. Advantageously, 7-acylaminocephalosporadesic acid, preferably as an alkali metal salt, is added directly to the solution containing the azolide.

Any amino, hydroxy, thiol or carboxy groups in the 7-acylaminocephalosporadesic acid or azolide reactants of the method of this invention are protected during the reaction by standard protecting groups. For example, t-butoxycarbonyl may be used to protect amino groups or trichloroethoxycarbonyl to protect amino, hydroxy and thiol groups. Carboxy groups may be protected by converting to the t-butyl ester. The protecting groups are removed after the O-acylation by standard procedures. For example, a t-butoxycarbonyl group on an amino group may be removed by treating with an acid such as trifluoroacetic acid and neutralizing the resulting salt, the trichloroethoxycarbonyl group may be removed by treating with zinc and acetic acid and the t-butyl ester may be hydrolyzed by treating with trifluoroacetic acid.

Other protecting groups may be used such as trityl to protect amino groups; the trityl group may be removed by treating with acid. Trimethylsilyl may be used to protect hydroxy or thiol groups in $R_2$. Also, hydroxy groups may be protected by tetrahydropyranyl groups and thiol groups may be protected with p-methoxybenzyl. The trimethylsilyl and tetrahydropyranyl protecting groups may be removed by treating with aqueous acid. p-Methoxybenzyl groups may be removed using trifluoroacetic acid.

The 7-acylaminocephalosporadesic acids or Formula I are prepared by methods known to the art, for example, by enzymatic hydrolysis of 7-acylaminocephalosporanic acids or by N-acylation of 7-aminocephalosporadesic acid.

The O-acyl-7-acylaminocephalosporadesic compounds of this invention are represented by Formula III above in which:

$R_1$ is 2-trienylmethyl, 4-pyridylthiomethyl, cyanomethyl, tetrazolylmethyl, sydnone-3-methyl, α-hydroxybenzyl, α-hydroxy-2-thienylmethyl, α-aminobenzyl, α-aminocyclohexa-1,4-dienylmethyl or α-amino-2-thienylmethyl;

$R_2$ is $CH_2(CH_2)_n$—O—$R_3$ or

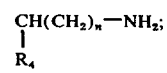

$R_3$ is methyl or ethyl;
$R_4$ is hydrogen, phenyl, benzyl or lower alkyl, optionally substituted by a lower alkylthio, mercapto, hydroxy, carboxy or amino substituent;
$n$ is 0–3 and
M is hydrogen, an alkali metal cation or a quaternary ammonium cation.

Preferred compounds of Formula III are those where $R_1$ is as defined above and

is an acyl group derived from an alkoxyalkanoic acid such as methoxyacetic, β-methoxypropionic, γ-methoxybutyric, or δ-methoxyvaleric acid or an amino acid such as glycine, phenylglycine, alanine, phenylalanine, methionine, cysteine, lysine, serine, aspartic acid, β-alanine, γ-aminobutyric acid or δ-aminovaleric acid.

Advantageous compounds of Formula III are, for example, the following:
 O-methoxyacetyl-7-(2-thienylacetamido)cephalosporadesic acid
 O-γ-methoxybutyryl-7-(α-aminphenylacetamido)-cephalosporadesic acid
 O-glycyl-7-(2-thienylacetamido)cephalosporadesic acid
 O-cysteinyl-7-(2-thienylacetamido)cephalosporadesic acid
 O-β-alanyl-7-(α-aminophenylacetamido)cephalosporadesic acid.

Cephalosporins having antibacterial activity are prepared by the process of this invention. The compounds, including the compounds of this invention, have activity against Gram-positive and Gram-negative bacteria. Exemplary of the microorganisms against which they are effective are *Staphylococcus aureus, Escherichia coli, Klebsiella pneumoniae, Streptococcus pyogenes* and *Streptococcus faecalis*. These cephalosporins are formulated for use and used to treat and prevent bacterial infections by standard procedures.

The following examples are not limiting but are illustrative of the method of this invention.

EXAMPLE 1

General Procedure

To 0.012 mole of a carboxylic acid in about 20 ml. of dry N,N-dimethylformamide is added 0.012 mole of a diazolide of carbonic acid. After stirring for from 0.5 to 1.5 hours, 0.010 mole of the appropriate 7-acylaminocephalosporadesic acid, preferably in the form of an alkali metal salt, is added either as a solid or in N,N-dimethylformamide solution. The progress of the reaction is monitored by thin-layer chromatography. When the reaction has reached completion, the mixture is poured into from 0.5 to 2.0 l. of ether, and the insoluble alkali metal salt of the O-acyl-7-acylaminocephalosporadesic acid is filtered off. The product is decolorized with charcoal and recrystallized. The product is separated from any unreacted 7-acylaminocephalosporadesic acid salt by converting the latter to the corresponding 7-acylaminocephalosporanolactone by mild acid treatment of the mixture (e.g. stirring a methanol solution with an acidic ion-exchange resin such as Amberlite IR-120H), then converting the product back into the alkali metal salt form which is separated from the lactone by recrystallization.

The alkali metal salt is converted to the O-acyl-7-acylaminocephalosporadesic acid by mild acid treatment. For example, an acidic ion-exchange resin may be used.

EXAMPLE 2

By the procedure of Example 1, using the following carboxylic acids:
 acetic acid
 propionic acid
 butyric acid
N,N'-carbonyldiimidazole and 7-(2-thienylacetamido)-cephalosporadesic acid, the following products are obtained, respectively:
 7-(2-thienylacetamido)cephalosporanic acid
 O-propionyl-7-(2-thienylacetamido)cephalosporadesic acid
 O-butyryl-7-(2-thienylacetamido)cephalosporadesic acid.

EXAMPLE 3

To 1.09 g. of methoxyacetic acid in 20 ml. of dry N,N-dimethylformamide is added 1.96 g. of N,N'-carbonyldiimidazole in one portion as a solid. After stirring for 30 minutes, 3.76 g. of sodium 7-(2-thienylacetamido)cephalosporadesate is added as a solid. The progress of the reaction is monitored by thin-layer chromatography using fluorescent silica gel plates and an 80:20:3 chloroformmethanol-formic acid solvent system. The reaction mixture is stirred for 26 hours, then poured into 1 liter of ether and filtered. The solid obtained is dissolved in wet methanol, charcoal is added and the mixture is stirred for about 30 minutes, then filtered. The resulting solution is concentrated and acetone is slowly added. After refrigerating for 3 days and then filtering, sodium O-methoxyacetyl-7-(2-thienylacetamido)cephalosporadesate hemihydrate is obtained.

| | $C_{17}H_{17}N_2O_7S_2Na . 1/2 H_2O$ (457.461) | |
|---|---|---|
| | Theory | Found |
| C | 44.63 | 44.55 |
| H | 3.96 | 4.05 |
| N | 6.12 | 6.05 |

This product has antibacterial activity, in particular against *Escherichia coli*.

Dissolving sodium O-methoxyacetyl-7-(2-thienylacetamido)cephalosporadesate hemihydrate in methanol, then stirring the solution with an excess of an acidic ion-exchange resin, filtering and removing the solvent in vacuo gives O-methoxyacetyl-7-(2-thienylacetamido)cephalosporadesic acid.

EXAMPLE 4

To 1.84 g. of N-t-butoxycarbonylglycine in 10 ml. of dry N,N-dimethylformamide is added 1.70 g. of N,N'-carbonyldiimidazole in one portion as a solid. After stirring for 30 minutes, 3.28 g. of sodium 7-(2-thienylacetamido)cephalosporadesate is added as a solid. The progress of the reaction is monitored by thin-layer chromatography using fluorescent silica gel plates and an 8:2:1 chloroformisopropanol-formic acid solvent system. The reaction mixture is stirred for 45 hours, then poured into 1 liter of ether and filtered. The solid obtained is dissolved in methanol and decolorized with charcoal. The solution is concentrated to about 75 ml. and diluted with 225 ml. of ether. The resulting gel is filtered off, then dissolved in methanol and stirred with an excess of an acidic ion-exchange resin. After filtering off the resin, the solvent is removed in vacuo to give O-(N-t-butoxycarbonylglycyl)-7-(2-thienylacetamido)-cephalosporadesic acid.

Treating an ether-acetone solution of O-(N-t-butoxycarbonylglycyl)-7-(2-thienylacetamido)cephalosporadesic acid with 30% sodium 2-ethylhexanoate in isopropanol gives the sodium salt hemihydrate.

|   | $C_{21}H_{24}N_3O_8S_2Na \cdot 1/2 H_2O$ (542.567) | |
|---|---|---|
|   | Theory | Found |
| C | 46.49 | 46.49 |
| H | 4.64 | 4.67 |
| N | 7.74 | 7.68 |

This product has antibacterial activity against Gram-positive and Gram-negative bacteria, in particular against *Staphylococcus aureus*, *Escherichia coli*, *Klebsiella pneumoniae*, *Streptococcus pyogenes* and *Streptococcus faecalis*.

To an ice-cooled flask equipped with a calcium sulfate drying tube and magnetic stirring and containing 20 ml. of trifluoroacetic acid is added 1.71 g. of O-(N-t-butoxycarbonylglycyl)-7-(2-thienylacetamido)cephalosporadesic acid. The reaction mixture is stirred in the ice bath for 1 hour and then allowed to warm to room temperature over 30 minutes. The mixture is then poured slowly into 250 ml. of rapidly stirred ether. The resulting solid is filtered off and dissolved in water containing a minimum amount of acetone. To the solution is added 5% aqueous sodium bicarbonate solution to raise the pH to 3.0. The resulting gel is filtered off, washed with water and then acetone and dried to give O-glycyl-7-(2-thienylacetamido)cephalosporadesic acid hydrate.

|   | $C_{16}H_{17}N_3O_6S_2 \cdot H_2O$ (429.484) | |
|---|---|---|
|   | Theory | Found |
| C | 44.75 | 44.85 |
| H | 4.46 | 4.37 |
| N | 9.74 | 9.21 |

This product has antibacterial activity, for example against *Staphylococcus aureus*, *Streptococcus pyogenes* and *Klebsiella pneumoniae*.

EXAMPLE 5 to 0.612 g. of pivalic acid in 15 ml. of dry N,N-dimethylformamide is added 0.972 g. of N,N'-carbonyldiimidazole. The mixture is stirred for 35 minutes, then 1.88 g. of sodium 7-(2-thienylacetamido)cephalosporadesate is added. The progress of the reaction is monitored by thin-layer chromatography using fluorescent silica gel plates and an 8:2:1 chloroform-isopropanol-formic acid solvent system. After 45 hours, the reaction mixture is poured into 700 ml. of ether. The resulting solid is filtered off and dissolved in methanol and decolorized with charcoal. The methanol is removed in vacuo, and wet acetone is added to the residue. The insoluble material is filtered off. The filtrate is evaporated to dryness in vacuo, and the residue is taken up in wet methanol. The solution is treated with acidic ion-exchange resin, filtered and stripped to dryness in vacuo. Ethyl acetate is added to the residue. The resulting solution is allowed to stand overnight. Ether is added to the solution, and the insoluble material is filtered off. The filtrate is treated with a 30% solution of sodium 2-ethylhexanoate in isopropanol. The precipitate is filtered off and dissolved in wet acetone. The solution is evaporated to dryness in vacuo to give sodium O-pivaloyl-7-(2-thienylacetamido)cephalosporadesate hydrate.

|   | $C_{19}H_{21}N_2O_6S_2Na \cdot H_2O$ (478.532) | |
|---|---|---|
|   | Theory | Found |
| C | 47.69 | 47.98 |
| H | 4.84 | 4.67 |
| N | 5.85 | 5.78 |

This product has antibacterial activity, for example against *Staphylococcus aureus*, *Streptococcus pyogenes* and *Diplococcus pneumoniae*.

The above prepared sodium salt is dissolved in methanol and treated with acidic ion-exchange resin to give, after filtering and removing the solvent in vacuo. O-pivaloyl-7-(2-thienylacetamido)cephalosporadesic acid hydrate.

EXAMPLE 6

Using benzoic acid, N,N'-carbonyldi-(1,2,4-triazole) and potassium 7-(2-thienylacetamido)cephalosporadesate in the procedure of Example 1, the product is O-benzoyl-7-(2-thienylacetamido)cephalosporadesic acid.

EXAMPLE 7

Using benzoic acid, N,N'-carbonyldiimidazole and benzyltrimethylammonium 7-(2-benzofurylacetamido)cephalosperadesate [prepared by treating potassium 7-(2-benzofurylacetamido)cephalosporadesate with an acidic ion-exchange resin and treating the resulting 7-(2-benzofurylacetamido)cephalosporadesic acid with benzyltrimethylammonium hydroxide] in the procedure of Example 1, the product is O-benzeyl-7-(2-benzofurylacetamido)cephalosporadesic acid.

Similarly, using benzyltrimethylammonium 7phenylthioacetamidocephalosporadesate (prepared by treating potassium 7-phenylthioacetamidocephalosporadesate with an acidic ion-exchange resin and treating the resulting 7-phenylthioacetamidocephalosporadesic acid with benzyltrimethylammonium hydroxide), the product is O-benzoyl-7-phenylthioacetamidocephalosporadesic acid.

EXAMPLE 8

Using 2-thiophenecarboxylic acid, N,N'-carbonyldiimidazole and potassium 7-(2-thienylacetamido)-cephalosporadesate in the procedure of Example 1, the product is O-(2-thenoyl)-7-(2-thienylacetamido)cephalosporadesic acid.

Similarly, using 2-furoic acid, N,N'-carbonyldiimidazole and potassium 7-phenylthioacetamidocephalosporadesate, the product is O-(2-furoyl)-7-phenylthioacetamidocephalosporadesic acid.

By the same procedure, using 2-naphthoic acid, N,N'-carbonyldiimidazole and potassium 7-phenylthioacetamidocephalosporadesate, the product is O-(2-naphthoyl)-7-phenylthioacetamidocephalosporadesic acid.

EXAMPLE 9

By the procedure of Example 1, the reaction of propionic acid, N,N'-carbonyldiimidazole and 7-phenylacetamidocephalosporadesic acid gives 7-phenylacetamido-O-propionylcephalosporadesic acid.

Similarly, using in place of propionic acid, the following:
  hexanoic acid
  phenylacetic acid
the products are, respectively:
  O-hexanoyl-7-phenylacetamidocephalosporadesic acid
  7-phenylacetamido-O-phenylacetylcephalosporadesic acid.

EXAMPLE 10

By the procedure of Example 1, the reaction of benzoic acid, N,N'-carbonyldiimidazole and 7-(5-isothiazolylacetamido)cephalosporadesic acid gives O-benzoyl-7-(5-isothiazolylacetamido)cephalosporadesic acid.

EXAMPLE 11

According to the procedure of Example 1, propionic acid in N,N-dimethylformamide is allowed to react with N,N'-carbonyldiimidazole, then 7-(α-methoxy-3,4-dichlorophenylacetamido)cephalosporadesic acid, as the sodium salt, is added and the reaction mixture is stirred until thin-layer chromatography shows the reaction is complete. The reaction mixture is then poured into ether and filtered to give, after working up by the procedure of Example 1, 7-(α-methoxy-3,4-dichlorophenylacetamido)-O-propionylcephalosporadesic acid.

EXAMPLE 12

To a solution of 25 g. of D-mandelic acid and 40 g. of N,N-dimethylaniline in 250 ml. of dry chloroform at −5° C. is added dropwise 38 g. of 2,2,2-trichloroethyl chloroformate. The reaction mixture is stirred at 0° C. for 1 hour, then washed at 0° C. with 375 ml. of 1N hydrochloric acid and then with 250 ml. of water. The reaction mixture is then extracted several times at 0° C. with a total of 1 liter of 5% aqueous sodium bicarbonate solution. The bicarbonate extract is washed with 150 ml. of ether and then acidified in the cold with 3N hydrochloric acid to precipitate O-(2,2,2-trichloroethoxycarbonyl)-D-mandelic acid, m.p. 157°–158° C.

A suspension of 4.26 g. of O-(2,2,2-trichloroethoxycarbonyl)-D-mandelic acid in 47 g. of thionyl chloride is heated at reflux for 4 hours. The excess thionyl chloride is removed in vacuo to leave solid O-(2,2,2-trichloroethoxycarbonyl)-D-mandeloyl chloride, m.p. 75°–77° C.

A solution of 7-aminocephalosporanic acid in a mixture of acetone and aqueous sodium bicarbonate is treated with O-(2,2,2-trichloroethoxycarbonyl)-D-mendeloyl chloride to give 7-[O-(2,2,2-trichloroethoxycarbonyl)-D-mandelamido]cephalosporanic acid. The sodium salt is prepared by treating with sodium 2-ethylhexanoate.

Sodium 7-[O-(2,2,2-trichloroethoxycarbonyl)-D-mandelamido]cephalosporadesate (6.0 g.), obtained by enzymatic deacetylation of sodium 7-[O-(2,2,2-trichloroethoxycarbonyl)-D-mandelamido]cephalosporanate, is allowed to react with 1.5 g. of N-propionylimidazole in 20 ml. of dry N,N-dimethylformamide, and the reaction mixture is worked up according to the procedure of Example 1 to give O-propionyl-7-[O-(2,2,2-trichloroethoxycarbonyl)-D-mandelamido]-cephalosporadesic acid.

A suspension of 0.60 g. of activated zinc dust in 6.0 ml. of 60% aqueous acetic acid is stirred for 15 minutes, and 0.60 g. of O-propionyl-7-[O-(2,2,2-trichloroethoxycarbonyl)-D-mandelamido]cephalosporadesic acid is added. The reaction mixture is stirred for 3 hours, then diluted with 20 ml. of water and filtered. The solid is washed with 50% aqueous acetic acid. The filtrate is acidified to pH 1.5 with 3N hydrochloric acid and extracted with ethyl acetate. The ethyl acetate extract is stripped to dryness in vacuo and the residue triturated with ether to give O-propionyl-7-(D-mandelamido)cephalosporadesic acid.

Similarly, using N-benzoylimidazole in place of N-propionylimidazole, the product is O-benzoyl-7-(O-mandelamido)cephalosporadesic acid.

EXAMPLE 13

By the procedure of Example 1, the reaction of a lower alkanoic acid, N,N'-carbonyldiimidazole and sodium 7-[α-(t-butoxycarbonylamino)-1,4-cyclohexadienylacetamido]cephalosporadesate, obtained by converting 7-[D-α-(t-butoxycarbonylamino)-1,4-cyclohexadienylacetamido]cephalosporanic acid to the sodium salt and subjecting the salt to enzymatic hydrolysis, gives 7-[D-α-(t-butoxycarbonylamino)-1,4-cyclohexadienylacetamido]-O-lower alkanoylcephalosporadesic acid.

Treating the product with trifluoroacetic acid by the procedure of Example 4 gives 7-(D-α-amino-1,4-cyclohexadienylacetamido)-O-lower alkanoylcephalosporadesic acid.

EXAMPLE 14

By the procedure of Example 1, the reaction of propionic acid, N,N'-carbonyldiimidazole and sodium 7-[D-α-(t-butoxycarbonylamino)phenylacetamido]cephalosporadesate, obtained by converting 7-[D-α-(t-butoxycarbonylamino)phenylacetamido]cephalosporanic acid to the sodium salt and subjecting the salt to enzymatic hydrolysis, gives 7-[D-α-(t-butoxycarbonylamino)phenylacetamido]-O-propionylcephalosporadesic acid.

A mixture of 7-[D-α-(t-butoxycarbonylamino)-phenylacetamido]-O-propionylcephalosporadesic acid and trifluoroacetic acid is stirred in an ice bath for 1 hour, then is allowed to warm to room temperature over 30 minutes. The mixture is then poured slowly into ether with rapid stirring to give, after working up by the procedure of Example 4, 7-(D-α-aminophenylacetamido)-O-propionylcephalosporadesic acid.

EXAMPLE 15

Using 2-furoic acid, N,N'-carbonyldiimidazole and sodium 7-phenoxyacetamidocephalosporadesate in the procedure of Example 1, the product is O-(2-furoyl)-7-phenoxyacetamidocephalosporadesic acid.

EXAMPLE 16

Using, in the procedure of Example 1, propionic acid, N,N'-carbonyldiimidazole and sodium 7-(1-tetrazolylacetamido)cephalosporadesate, prepared by converting 7-(1-tetrazolylacetamido)cephalosporanic acid to the sodium salt and then subjecting it to enzymatic hydrolysis, the product is O-propionyl-7-(1-tetrazolylacetamido)cephalosporadesic acid.

By the same procedure, using sodium 7-(4-pyridylthioacetamido)cephalosporadesate, prepared by enzymatic hydrolysis of sodium 7-(4-pyridylthioacetamido)cephalosporante, the product is O-propionyl-7-(4-pyridylthioacetamido)cephalosporadesic acid.

EXAMPLE 17

Using N-t-butoxycarbonylmethionine, N,N'-carbonyldiimidazole and sodium 7-(2-thienylacetamido)-cephalosporadesate in the procedure of Example 4, O-methionyl-7-(2-thienylacetamido)cephalosporadesic acid is obtained.

EXAMPLE 18

Example 4 is followed using N-t-butoxycarbonyl-2,2-dimethylthiazolidine-4-carboxylic acid (R. B. Woodward et al., *J. Am. Chem. Soc.* 88:852, 1966), N,N'-carbonyldiimidazole and sodium 7-(2-thienylacetamido)-cephalosporadesate to give, after treatment with trifluoroacetic acid at room temperature, O-cysteinyl-7-(2-thienylacetamido)cephalosporadesic acid.

EXAMPLE 19

By the procedure of Example 4, the reaction of N-t-butoxycarbonyl-O-(2,2,2-trifluoro-1-benzyloxycarbonylaminoethyl)-L-serine (F. Weygard et al., *Chem. Ber.* 101:923, 1968), N,N'-carbonyldiimidazole and sodium 7-(2-thienylacetamido)cephalosporadesate gives O-[N-t-butoxycarbonyl-O-(2,2,2-trifluoro-1-benzyloxycarbonylaminoethyl)-L-seryl]-7-(2-thienylacetamido)cephalosporadesic acid. This product is treated with a mixture of trifluoroacetic acid and anisole containing one equivalent of HBr. The HBr salt is isolated and treated in aqueous solution with an anion-exchange resin in methyl isobutyl ketone to give O-(L-seryl)-7-(2-thienylacetamido)cephalosporadesic acid.

EXAMPLE 20

Using N-t-butoxycarbonylglycine, N,N'-carbonyldiimidazole and the appropriate sodium cephalosporadesate (prepared by enzymatic hydrolysis of the corresponding cephalosporanic acid) in the procedure of Example 4, the following products are obtained:
O-glycyl-7-(4-pyridylthioacetamide)cephalosporadesic acid
O-glycyl-7-cyanoacetamidocephalosporadesic acid
O-glycyl-7-(1-sydnoneacetamido)cephalosporadesic acid
O-glycyl-7-(3-sydoneacetamido)cephalosporadesic acid
O-glycyl-7-mandelamidocepahlosporadesic acid
O-glycyl-7-(α-hydroxythien-2-ylacetamido)cephalosporadesic acid
O-glycyl-7-(α-aminophenylacetamido)cephalosporadesic acid
O-glycyl-7-(α-amino-1,4-cyclohexadien-1-ylacetamido)cephalosporadesic acid
O-glycyl-7-(α-aminothien-2-ylacetamido)cephalosporadesic acid.

EXAMPLE 21

In the procedure of Example 4, using sodium 2-thienylacetamidocephalosporadesate, N,N'-carbonyldiimidazole and the appropriate amino acid, the amino group being suitably protected, the protecting group being later removed, the following products are obtained:
O-phenylglycyl-7-(2-thienylacetamido)cephalosporadesic acid
O-alanyl-7-(2-thienylacetamido)cephalosporadesic acid
O-phenylalanyl-7-(2-thienylacetamido)cephalosporadesic acid
O-aspartyl-7-(2-thienylacetamido)cephalosporadesic acid
O-lysyl-7-(2-thienylacetamido)cephalosporadesic acid
O-(β-alanyl)-7-(2-thienylacetamido)cephalosporadesic acid
O-(γ-aminobutyryl)-7-(2-thienylacetamido)cephalosporadesic acid
O-(δ-aminovaleryl)-7-(2-thienylacetamido)cephalosporadesic acid.

EXAMPLE 22

Using, in the procedure of Example 18, N-t-butoxycarbonyl-2,2-dimethylthiazolidine-4-carboxylic acid, N,N'-carbonyldiimidazole and the appropriate sodium 7-acylcephalosporadesate, the following products are obtained:
O-cysteinyl-7-(4-pyridylthioacetamido)cephalosporadesic acid
O-cysteinyl-7-cyanoacetamidocephalosporadesic acid
O-cysteinyl-7-(1-tetrazolylacetamido)cephalosporadesic acid
O-cysteinyl-7-(3-sydnoneacetamido)cephalosporadesic acid
O-cysteinyl-7-mandelamidocephalosporadesic acid
O-cysteinyl-7-(α-hydroxythien-2-ylacetamido)cephalosporadesic acid
O-cysteinyl-7-(α-aminophenylacetamido)cephalosporadesic acid
O-cysteinyl-7-(α-amino-1,4-cyclohexadien-1-ylacetamido)cephalosporadesic acid
O-cysteinyl-7-(α-aminothien-2-ylacetamido)cephalosporadesic acid.

EXAMPLE 23

Using N-t-butoxycarbonyl-O-(2,2,2-trifluoro-1-benzyloxycarbonylaminoethyl)-L-serine, N,N'-carbonyldiimidazole and the appropriate sodium 7-acylcephalosporadesate in the procedure of Example 19, the following products are obtained:
O-seryl-7-(4-pyridylthioacetamido)cephalosporadesic acid
O-seryl-7-cyanoacetamidocephalosporadesic acid
O-seryl-7-(1-tetrazolylacetamido)cephalosporadesic acid
O-seryl-7-(3-sydnoneacetamido)cephalosporadesic acid
O-seryl-7-mandelamidocepahlosporadesic acid
O-seryl-7-(α-hydroxythien-2-ylacetamido)cephalosporadesic acid
O-seryl-7-(α-aminophenylacetamido)cephalosporadesic acid
O-seryl-7-(α-amino-1,4-cyclohexadien-1-ylacetamido)cephalosporadesic acid
O-seryl-7-(α-aminothien-2-ylacetamido)cephalosporadesic acid.

EXAMPLE 24

By the procedure of Example 4, N-t-butoxycarbonylphenylglycine, N,N'-carbonyldiimidazole and the corresponding sodium 7-acylcephalosporadesate are reacted to give the following products:

O-phenylglycyl-7-(4-pyridylthioacetamido)cephalosporadesic acid
O-phenylglycyl-7-cyanoacetamidocephalosporadesic acid
O-phenylglycyl-7-(1-tetrazolylacetamido)cephalosporadesic acid
O-phenylglycyl-7-(3-sydnoneacetamido)cephalosporadesic acid
O-phenylglycyl-7-mandelamidocephalosporadesic acid
O-phenylglycyl-7-(α-hydroxythien-2-ylacetamido)-cephalosporadesic acid
O-phenylglycyl-7-(α-aminophenylacetamido)cephalosporadesic acid
O-phenylglycyl-7-(α-amino-1,4-cyclohexadien-1-ylacetamido)cephalosporadesic acid
O-phenylglycyl-7-(α-aminothien-2-ylacetamido)-cephalosporadesic acid.

EXAMPLE 25

Using N-t-butoxycarbonylalanine, N,N'-carbonyldiimidazole and the appropriate sodium 7-acylcephalosporadesate according to the procedure of Example 4, the following products are obtained:

O-alanyl-7-(4-pyridylthioacetamido)cephalosporadesic acid
O-alanyl-7-cyanoacetamidocephalosporadesic acid
O-alanyl-7-(1-tetrazolylacetamido)cephalosporadesic acid
O-alanyl-7-(3-sydnoneacetamido)cephalosporadesic acid
O-alanyl-7-mandelamidocephalosporadesic acid
O-alanyl-7-(α-hydroxythien-2-ylacetamido)cephalosporadesic acid
O-alanyl-7-(α-aminophenylacetamido)cephalosporadesic acid
O-alanyl-7-(α-amino-1,4-cyclohexadien-1-ylacetamido)cephalosporadesic acid
O-alanyl-7-(α-aminothien-2-ylacetamido)cephalosporadesic acid.

EXAMPLE 26

Using N-t-butoxycarbonylphenylalanine, N,N-carbonyldiimidazole and the appropriate sodium 7-acylcephalosporadesate according to the procedure of Example 4, the following products are obtained:

O-phenylalanyl-7-(4-pyridylthioacetamido)cephalosporadesic acid
O-phenylalanyl-7-cyanoacetamidocephalosporadesic acid
O-phenylalanyl-7-(1-tetrazolylacetamido)cephalosporadesic acid
O-phenylalanyl-7-(3-sydnoneacetamido)cephalosporadesic acid
O-phenylalanyl-7-mandelamidocephalosporadesic acid
O-phenylalanyl-7-(α-hydroxythien-2-ylacetamido)-cephalosporadesic acid
O-phenylalanyl-7-(α-aminophenylacetamido)cephalosporadesic acid
O-phenylalanyl-7-(α-amino-1,4-cyclohexadien-1-ylacetamido)cephalosporadesic acid
O-phenylalanyl-7-(α-aminothien-2-ylacetamido)-cephalosporadesic acid.

EXAMPLE 27

Using N-t-butoxycarbonylmethionine, N,N'-carbonyldiimidazole and the appropriate sodium 7-acylcephalosporadesate according to the procedure of Example 4, the following products are obtained:

O-methionyl-7-(4-pyridylthioacetamido)cephalosporadesic acid
O-methionyl-7-cyanoacetamidocephalosporadesic acid
O-methionyl-7-(1-tetrazolylacetamido)cephalosporadesic acid
O-methionyl-7-(3-sydnoneacetamido)cephalosporadesic acid
O-methionyl-7-mandelamidocephalosporadesic acid
O-methionyl-7-(α-hydroxythien-2-ylacetamido)-cephalosporadesic acid
O-methionyl-7-(α-aminophenylacetamido)cephalosporadesic acid
O-methionyl-7-(α-amino-1,4-cyclohexadien-1-ylacetamido)cephalosporadesic acid
O-methionyl-7-(α-aminothien-2-ylacetamido)cephalosporadesic acid.

EXAMPLE 28

Using N,N-di-t-butoxycarbonyllysine, N,N'-carbonyldiimidazole and the appropriate sodium 7-acylcephalosporadesate according to the procedure of Example 4, the following products are obtained:

O-lysyl-7-(4-pyridylthioacetamido)cephalosporadesic acid
O-lysyl-7-cyanoacetamidocephalosporadesic acid
O-lysyl-7-(1-tetrazolylacetamido)cephalosporadesic acid
O-lysyl-7-(3-sydnoneacetamido)cephalosporadesic acid
O-lysyl-7-mandelamidocephalosporadesic acid
O-lysyl-7-(α-hydroxythien-2-ylacetamido)cephalosporadesic acid
O-lysyl-7-(α-aminophenylacetamido)cephalosporadesic acid
O-lysyl-7-(α-amino-1,4-cyclohexadien-1-ylacetamido)cephalosporadesic acid
O-lysyl-7-(α-aminothien-2-ylacetamido)cephalosporadesic acid.

EXAMPLE 29

Using N-t-butoxycarbonylaspartic acid β-t-butyl ester, N,N'-carbonyldiimidazole and the appropriate sodium 7-acylcephalosporadesate according to the procedure of Example 4, the following products are obtained:

O-aspartyl-7-(4-pyridylthioacetamido)cephalosporadesic acid
O-aspartyl-7-cyanoacetamidocephalosporadesic acid
O-aspartyl-7-(1-tetrazolylacetamido)cephalosporadesic acid
O-aspartyl-7-(3-sydnoneacetamido)cephalosporadesic acid
O-aspartyl-7-mandelamidocephalosporadesic acid
O-aspartyl-7-(α-hydroxythien-2-ylacetamido)cephalosporadesic acid
O-aspartyl-7-(α-aminophenylacetamido)cephalosporadesic acid
O-aspartyl-7-(α-amino-1,4-cyclohexadien-1-ylacetamido)cephalosporadesic acid O-aspartyl-7-(α-aminothien-2-ylacetamido)cephalosporadesic acid.

EXAMPLE 30

Using N-t-butoxycarbonyl-β-alanine, N,N'-carbonyldiimidazole and the appropriate sodium 7-acylcephalosporadesate according to the procedure of Example 4, the following products are obtained:
- O-(β-alanyl)-7-(4-pyridylthioacetamido)cephalosporadesic acid
- O-(β-alanyl)-7-cyanoacetamidocephalosporadesic acid
- O-(β-alanyl)-7-(1-tetrazolylacetamido)cephalosporadesic acid
- O-(β-alanyl)-7-(3-sydnoneacetamido)cephalosporadesic acid
- O-(β-alanyl)-7-mandelamidocephalosporadesic acid
- O-(β-alanyl)-7-(α-hydroxythien-2-ylacetamido)cephalosporadesic acid
- O-(β-alanyl)-7-(α-aminophenylacetamido)cephalosporadesic acid
- O-(β-alanyl)-7-(α-amino-1,4-cyclohexadien-1-ylacetamido)cephalosporadesic acid
- O-(β-alanyl)-7-(α-aminothien-2-ylacetamido)cephalosporadesic acid.

EXAMPLE 31

Using N-t-butoxycarbonyl-γ-aminobutric acid, N,N'-carbonyldiimidazole and the appropriate sodium 7-acylcephalosporadesate according to the procedure of Example 4, the following products are obtained:
- O-(γ-aminobutyryl)-7-(4-pyridylthioacetamido)-cephalosporadesic acid
- O-(γ-aminobutyryl)-7-cyanoacetamidocephalosporadesic acid
- O-(γ-aminobutyryl)-7-(1-tetrazolylacetamido)cephalosporadesic acid
- O-(γ-aminobutyryl)-7-(3-sydnoneacetamido)cephalosporadesic acid
- O-(γ-aminobutyryl)-7-mandelamidocephalosporadesic acid
- O-(γ-aminobutyryl)-7-(α-hydroxythien-2-ylacetamido)cephalosporadesic acid
- O-(γ-aminobutyryl)-7-(α-aminophenylacetamido)-cephalosporadesic acid
- O-(γ-aminobutyryl)-7-(α-amino-1,4-cyclohexadien-1-ylacetamido)cephalosporadesic acid
- O-(γ-aminobutyryl)-7-(α-aminothien-2-ylacetamido)cephalosporadesic acid.

EXAMPLE 32

Using N-t-butoxycarbonyl-δ-aminovaleric acid, N,N'-carbonyldiimidazole and the appropriate sodium 7-acylcephalosporadesate according to the procedure of Example 4, the following products are obtained:
- O-(δ-aminovaleryl)-7-(4-pyridylthioacetamido)-cephalosporadesic acid
- O-(δ-aminovaleryl)-7-cyanoacetamidocephalosporadesic acid
- O-(δ-aminovaleryl)-7-(1-tetrazolylacetamido)cephalosporadesic acid
- O-(δ-aminovaleryl)-7-(3-sydnoneacetamido)cephalosporadesic acid
- O-(δ-aminovaleryl)-7-mandelamidocephalosporadesic acid
- O-(δ-aminovaleryl)-7-(α-hydroxythien-2-ylacetamido)cephalosporadesic acid
- O-(δ-aminovaleryl)-7-(α-aminophenylacetamido)-cephalosporadesic acid
- O-(δ-aminovaleryl)-7-(α-amino-1,4-cyclohexadien-1-ylacetamido)cephalosporadesic acid
- O-(δ-aminovaleryl)-7-(α-aminothien-2-ylacetamido)cephalosporadesic acid.

EXAMPLE 33

Using methoxyacetic acid, N,N'-carbonyldiimidazole and the appropriate sodium 7-acylaminocephalosporadesate according to the procedure of Example 3, the following products are obtained:
- O-methoxyacetyl-7-(4-pyridylthioacetamido)cephalosporadesic acid
- O-methoxyacetyl-7-cyanoacetamidocephalosporadesic acid
- O-methoxyacetyl-7-(1-tetrazolylacetamido)cephalosporadesic acid
- O-methoxyacetyl-7-(3-sydnoneacetamido)cephalosporadesic acid
- O-methoxyacetyl-7-mandelamidocephalosporadesic acid
- O-methoxyacetyl-7-(α-hydroxythien-2-ylacetamido)cephalosporadesic acid
- O-methoxyacetyl-7-(α-aminophenylacetamido)-cephalosporadesic acid
- O-methoxyacetyl-7-(α-amino-1,4-cyclohexadien-1-ylacetamido)cephalosporadesic acid
- O-methoxyacetyl-7-(α-aminothien-2-ylacetamido)-cephalosporadesic acid.

EXAMPLE 34

Using β-methoxypropionic acid, N,N'-carbonyldiimidazole and the appropriate sodium 7-acylaminocephalosporadesate according to the procedure of Example 3, the following products are obtained:
- O-β-methoxypropionyl-7-(2-thienylacetamido)cephalosporadesic acid
- O-β-methoxypropionyl-7-(4-pyridylthioacetamido)-cephalosporadesic acid
- O-β-methoxypropionyl-7-cyanoacetamidocephalosporadesic acid
- O-β-methoxypropionyl-7-(1-tetrazolylacetamido)-cephalosporadesic acid
- O-β-methoxypropionyl-7-(3-sydnoneacetamido)-cephalosporadesic acid
- O-β-methoxypropionyl-7-mandelamidocephalosporadesic acid
- O-β-methoxypropionyl-7-(α-hydroxythien-2-ylacetamido)cephalosporadesic acid
- O-β-methoxypropionyl-7-(α-aminophenylacetamido)cephalosporadesic acid
- O-β-methoxypropionyl-7-(α-amino-1,4-cyclohexadien-1-ylacetamido)cephalosporadesic acid
- O-β-methoxypropionyl-7-(α-aminothien-2-ylacetamido)cephalosporadesic acid.

EXAMPLE 35

Using γ-methoxybutyric acid, N,N'-carbonyldiimidazole and the appropriate sodium 7-acylaminocephalosporadesate according to the procedure of Example 3, the following products are obtained:
- O-γ-methoxybutyryl-7-(2-thienylacetamido)cephalosporadesic acid
- O-γ-methoxybutyryl-7-(4-pyridylthioacetamido)-cephalosporadesic acid O-γ-methoxybutyryl-7-cyanoacetamidocephalosporadesic acid O-γ-methoxybutyryl-7-(1-tetrazolylacetamido)cephalosporadesic acid O-γ-methoxybutyryl-7-(3-sydnoneacetamido)cephalosporadesic acid O-γ-methoxybutyryl-7-mandelamidocephalosporadesic acid O-γ-methoxybutyryl-7-(α-hydroxythien-2-ylacetamido)cephalosporadesic acid O-γ-methoxybutyryl-7-(α-aminophenylacetamido)-cephalosporadesic acid O-γ-methoxybutyryl-7-(α-amino-1,4-cyclohexadien-1-ylacetamido)cephalosporadesic acid O-γ-methoxybutyryl-7-(α-aminothien-2-ylacetamido)cephalosporadesic acid.

EXAMPLE 36

Using δ-methoxyvaleric acid, N,N'-carbonyldiimidazole and the appropriate sodium 7-acylcephalosporadesate according to the procedure of Example 3, the following products are obtained:

O-δ-methoxyvaleryl-7-(2-thienylacetamido)cephalosporadesic acid

O-δ-methoxyvaleryl-7-(4-pyridylthioacetamido)-cephalosporadesic acid

O-δ-methoxyvaleryl-7-cyanoacetamidocephalosporadesic acid

O-δ-methoxyvaleryl-7-(1-tetrazolylacetamido)cephalosporadesic acid

O-δ-methoxyvaleryl-7-(3-sydnoneacetamido)cephalosporadesic acid

O-δ-methoxyvaleryl-7-mandelamidocephalosporadesic acid

O-δ-methoxyvaleryl-7-(α-hydroxythien-2-ylacetamido)cephalosporadesic acid

O-δ-methoxyvaleryl-7-(α-aminophenylacetamido)-cephalosporadesic acid

O-δ-methoxyvaleryl-7-(α-amino-1,4-cyclohexadien-1-ylacetamido)cephalosporadesic acid O-δ-methoxyvaleryl-7-(α-aminothien-2-ylacetamido)cephalosporadesic acid.

EXAMPLE 37

When α-ethoxyacetic acid, β-ethoxypropionic acid, γ-ethoxybutyric acid or δ-ethoxyvaleric acid are substituted for the methoxyalkanoic acids in Examples 33–36, respectively, the corresponding O-ethoxyalkanoyl-7-acylaminocephalosporadesic acids are obtained.

What is claimed is:

1. A compound of the formula:

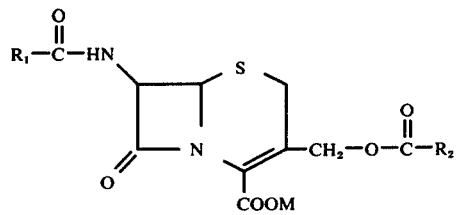

in which:

$R_1$ is 2-thienylmethyl, 4-pyridylthiomethyl, cyanomethyl, tetrazolylmethyl, sydnone-3-methyl, α-hydroxybenzyl, α-hydroxy-2-thienylmethyl, α-aminobenzyl, α-aminocyclohexa-1,4-dienylmethyl or α-amino-2-thienylmethyl;

$R_2$ is

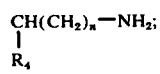

$R_4$ is hydrogen, phenyl, benzyl or lower alkyl, optionally substituted by a lower alkylthio, mercapto, hydroxy, carboxy or amino substituent;

$n$ is 0–3 and

M is hydrogen, an alkali metal cation or a quaternary ammonium cation.

2. A compound of claim 1 where

is glycyl, phenylglycyl, alanyl, phenylalanyl, methionyl, cysteinyl, lysyl, seryl, aspartyl, β-alanyl, γ-aminobutyryl or δ-aminovaleryl.

3. A compound of claim 1 being the compound O-glycyl-7-(2-thienylacetamido)cephalosporadesic acid.

4. A compound of claim 1 being the compound O-cysteinyl-7-(2-thienylacetamido)cephalosporadesic acid.

5. A compound of claim 1 being the compound O-β-alanyl-7-(α-aminophenylacetamido)cephalosporadesic acid.

* * * * *

UNITED STATES PATENT AND TRADEMARK OFFICE
CERTIFICATE OF CORRECTION

PATENT NO. : 4,007,178
DATED : February 8, 1977
INVENTOR(S) : David A. Berges

It is certified that error appears in the above-identified patent and that said Letters Patent are hereby corrected as shown below:

Column 1, line 13, "0-acyl-Lb 7-" should read
-- 0-acyl-7- -- .

Column 2, line 30 should read $$-N\bigcirc$$

Column 2, line 59, "substituted-" should read
-- a substituted- -- .

Column 4, line 52, "60" should read -- α -- .

Signed and Sealed this

Third Day of May 1977

[SEAL]

Attest:

RUTH C. MASON
Attesting Officer

C. MARSHALL DANN
Commissioner of Patents and Trademarks